United States Patent [19]

Robyt et al.

[11] 4,228,150

[45] Oct. 14, 1980

[54] METHOD OF INHIBITING DEXTRANSUCRASE AND ORAL COMPOSITIONS FOR USE THEREIN

[75] Inventors: John F. Robyt; John N. Zikopoulos, both of Ames, Iowa

[73] Assignee: Iowa State University Research Foundation, Inc., Ames, Iowa

[21] Appl. No.: 32,398

[22] Filed: Apr. 23, 1979

[51] Int. Cl.$^2$ .......................... A61K 9/68; A61K 7/18; A61K 31/70

[52] U.S. Cl. ......................................... 424/48; 127/29; 127/30; 424/52; 424/180; 426/39; 426/74; 426/658; 426/660; 435/184; 435/193

[58] Field of Search ..................... 536/122; 424/48, 52, 424/180; 195/122, 123; 426/39, 74, 658, 660; 127/29, 30

[56] References Cited

U.S. PATENT DOCUMENTS

| | | | |
|---|---|---|---|
| 2,365,776 | 12/1944 | Raymond et al. | 536/122 X |
| 2,684,961 | 7/1954 | Barham | 536/122 |
| 2,927,058 | 3/1960 | Minto | 536/122 X |

FOREIGN PATENT DOCUMENTS 959407  6/1964  United Kingdom .................... 536/122

OTHER PUBLICATIONS

Jung, Stephanie May, "Mechanistics Studies on the Dextran Sucrase of Streptococcus Sanguis ATCC 10558:Alpha 1-Fluoroglucose as a Substrate for the Enzyme", 273 p. (1977) from Diss. Abstr. Int. B (1978) 38(11):5337-5338, Univ. Microfilm into Order 7805862.
Jung S. M., Mayer R. M., Fed. Proc. (Fepra)36(3)(1977):931, "The Utilization of 1 Fluoroglucose as a Substitute for Dextran Sucrase".
Hough, L. et al., Nature London (1976):263(5580):800, "Enhancement in the Sweetness of Sucrose".

*Primary Examiner*—Shep K. Rose
*Attorney, Agent, or Firm*—Tilton, Fallon, Lungmus & Chestnut

[57] ABSTRACT

Dextransucrase synthesis of dextran from sucrose is inhibited by novel fluorosucroses which are substituted with fluorine for at least the $C_6$ hydroxyl, and which may also be substituted with fluorine for other hydroxyls. Oral compositions containing such fluorosucrose can be used to control dextran formation in the mouth. Dextran comprises the principal component of dental plaque.

26 Claims, No Drawings

METHOD OF INHIBITING DEXTRANSUCRASE AND ORAL COMPOSITIONS FOR USE THEREIN

GRANT REFERENCE

The invention described herein was made in the course of work under a grant from the Department of Health, Education, and Welfare, National Institute of Dental Research.

BACKGROUND AND PRIOR ART

Dextrans are high molecular weight polysaccharides of D-glucopyranose units that are synthesized from sucrose by the enzyme dextransucrase. It is known that a number of bacterial species belonging to the family Lactobacilleae elaborate a dextransucrase enzyme. Ubiquitous species of such bacteria include *Leuconostoc mesenteroides, Streptococcus mutans,* and *Streptococcus sanguis.* These and similar bacteria form dextran as an extra-cellular slime. Dextran synthesizing bacteria are commonly present in the mouth, growing on the gums and teeth. The elaborated dextransucrase forms dextran from the sucrose passing through the mouth with foods or drinks, resulting in sticky deposits on the teeth.

The deposited dextran results in the formation of dental plaque, which holds aggregates of carious producing bacteria, and is known to be undesirable by contributing to caries and periodontal disease. Gibbons et al., *Arch Oral Biol.,* 12:11 (1967); Gibbons et al., *Arch Oral. Biol.,* 13:1249 (1968); Gibbons et al., *J. Bacteriol.,* 98:341 (1969); and Scherp, *Science,* 173:1199 (1971).

It is recognized that a means for decomposing dextran or impeding its synthesis in the mouth would be of benefit in controlling plaque formation, and, ultimately, in mitigating caries and periodontal disease. See Scherp, *Science,* 173:1199, at 1202 (1971). In this connection, it was suggested that dextranase might be employed to decompose dextran formed in the mouth. Even if this should prove feasible, a more fundamental approach is to inhibit dextran synthesis, thereby avoiding the formation of plaque. Heretofore, however, no method has been known for inhibiting or controlling the action of dextransucrase, except to reduce or withhold sucrose from the diet. This is not easy to accomplish. It is difficult to avoid oral intake of sucrose in countries such as the United States where it is present in a wide varieties of foods and beverages. Moreover, sucrose is a natural constituent of many plant foods and, therefore, it would be expensive and impractical to completely eliminate it from normal diets.

The mechanism of action of dextransucrase has been described by Robyt et al., *Arch. Biochem. Biophys.,* 165:634 (1974). The mechanism postulates a glucosyl and a dextranosyl covalent enzyme intermediate. The glucose is obtained from sucrose and is incorporated into the growing dextran chain by a nucleophilic displacement of the $C_1$ of the reducing end of the dextranosyl chain by the $C_6$-hydroxyl of the glucosyl group forming a new $\alpha$-1,6 glucosidic linkage.

SUMMARY OF THE INVENTION

This invention is based on the discovery that the replacement of the $C_6$-hydroxyl group of sucrose by fluorine results in novel fluorosucrose compounds which can be employed to inhibit the dextransucrase synthesis of dextran from sucrose. While the mechanism of action is not known with certainty, it is probable that the fluoroglucose unit of fluorosucrose forms a covalent dead-end complex with dextransucrase, which blocks the action of the enzyme in the presence of surcose.

According to the mechanism proposed by Robyt et al (cited above), one of the reactions involves the nucleophilic attack by the $C_6$-hydroxyl oxygen of the covalently attached glucosyl unit onto the $C_1$ of the reducing end of the covalently attached dextran chain. The discovery of the inhibitory effect of 6-substituted fluorosucroses is consistent with this theory. The replacement of the $C_6$-hydroxyl group of the glucose unit of sucrose by a fluorine atom gives a 6-fluoroglucosyl complex with the enzyme. Because of the less nucleophilic character of the fluorine atom and its consequent inability to form an $\alpha$-1,6 glucosidic linkage, the fluoroglucose is not incorporated into dextran, and a covalent dead-end complex results with the enzyme. This dead-end complex cannot synthesize dextran, and thus the biosynthesis of dextran from sucrose by dextransucrase is prevented.

In the fluorination of sucrose the substitution of the primary hydroxyl groups ($C_6$, $C_{1'}$, and $C_{6'}$) is specific. One of the monosubstituted compounds is 6-fluorosucrose (6-deoxy-6-fluorosucrose), which is a preferred compound for use in practicing the inhibition of dextransucrase. However, the more highly fluorinated derivatives can also be employed, such as 6,1'-difluorosucrose (6,1'-dideoxy-6,1'-difluorosucrose), 6,6'-difluorosucrose (6,6'-dideoxy-6,6'-difluorosucrose), and 6,1',6'-trifluorosucrose (6,1',6'-trideoxy-6,1',6'-trifluorosucrose). While all of these compounds are inhibitory for dextransucrase, the critical substitution is the $C_6$-hydroxyl group with fluorine, which is present in all the designated fluorosucroses. It is particularly convenient that mixtures containing several of the active fluorosucroses can be synthesized and used as inhibitors without the need for separation of the compounds.

The method of the present invention has utility for inhibiting the dextransucrase synthesis of dextran from sucrose. By introducing the mixture of fluorosucroses into the oral cavity the enzymes can be effectively inhibited. By this procedure, the biosynthesis of dextran can be controlled or prevented. Thus, by combining the fluorosucroses with a carrier suitable for use in the oral cavity, such as toothpaste, mouthwash, or chewing gum, an oral vehicle is provided for the control of plaque formation in the mouth. With certain of the fluorosucroses, the levansucrase synthesis of levan from sucrose is also inhibited. This is believed to be desirable in minimizing the formation of dental plaque, which also contain levan, although in relatively small amounts compared to its dextran content.

All of the active fluorosucroses of this invention are believed to be novel compounds. Some corresponding chlorosucroses have been reported, but have not been recognized as inhibitors for dextran or levan biosynthesis; and, in fact, they appear to have little value for this purpose. For example, 6,1',6'-trichlorosucrose is relatively ineffective as an inhibitor for dextran as compared to 6,1',6'-trifluorosucrose.

DETAILED DESCRIPTION

The method of the present invention is practiced by introducing the fluorosucrose inhibitors into an aqueous solution of dextransucrase. A sufficient amount of the inhibitor is dissolved to effectively form dead-end complexes with the enzyme and, thus, prevent the synthesis of dextran from sucrose by dextransucrase. Experimental tests, as will be described in further detail below, have indicated that the inhibitory effects of the fluorosucroses become apparent at concentrations as low as 4 milligrams of the inhibitor per milliliter of water. An effective concentration range for obtaining substantially total inhibitiion is from 20 milligrams to 30 milligrams per milliliter. Higher concentrations can be used although they are not required. In practical applications, concentrations of the fluorosucrose inhibitors in water greater than 50 mg. per ml. will usually not be employed, except that temporarily higher concentrations may be used in the mouth, depending on the mode of administration of the inhibitor. The foregoing concentrations are on the basis of active inhibitor.

For control of dextran formation in the oral cavity, it is preferred to apply the fluorosucrose inhibitor in combination with a suitable carrier. The carrier may be water, a water solution of the fluorosucrose being prepared by the user as required. More desirably, however, the inhibitor may be dissolved in aqueous mouthwashes, which on use can serve the purposes of ordinary mouthwashes while providing the additional benefit of the dextran inhibition. Such aqueous solutions of aqueous mouthwashes can advantageously contain from 20 to 30 grams of the active fluorosucrose inhibitor per liter.

Other dental vehicles can be used for introducing the fluorosucrose inhibitor into the mouth. These include toothpaste and toothpowders. Based on the weight of the toothpaste or toothpowder, it may advantageously contain from 1 to 5% by weight of the active fluorosucrose inhibitors based on the total weight of the toothpaste or toothpowder.

Other carriers suitable for use in the oral cavity can be employed. These include water-soluble tablets and chewing gum. A single tablet or single stick of chewing gum may contain from 1 to 5% by weight of the active fluorosucrose inhibitor. The term "tablet" as used here refers not only to tablets formed by pressure tableting, but also to cast or molded tablets, sometimes referred to as a lozenge, such as cough drops.

While some fluorosucrose inhibitor will remain in the mouth after each treatment, such as each time the teeth are brushed or a mouthwash used, to provide the most effective control of dextran formation, repeated treatments at intervals of about 4 to 8 hours are desirable. For example, using a fluorosucrose-containing toothpaste or mouthwash in the morning, at supper time, and before bedtime, should provide reasonable effective control. For more frequent use, it may be convenient to employ the inhibitor in the form of tablets or chewing gum. These can advantageously be used at intervals of every 1 to 3 hours throughout the day, and can thereby provide even more effective control.

For purposes of the present invention, fluorine has been substituted for at least the $C_6$ primary hydroxyl, and some or all of the other primary hydroxyls ($C_{1'}$ and $C_{6'}$) of sucrose. Mixtures of such fluoroderivatives of sucrose can be employed, and it is not necessary to remove the inactive fluorosucrose compounds. The active compounds for dextransucrase synthesis inhibition are: 6-fluorosucrose (6-deoxy-6-fluorosucrose), 6,1'-difluorosucrose (6,1'-dideoxy-6-,1'-difluorosucrose), 6,6'-difluorosucrose (6,6'-dideoxy-6,6'-difluorosucrose), and 6,1',6'-trifluorosucrose (6,1',6'-trideoxy-6,1',6'-trifluorosucrose), all of which are $C_6$- substituted. Any of these compounds could also be used separately or in some combination. They all are believed to have approximately the same effectiveness on a weight basis. The amounts and concentrations to be used, therefore, have been set out above on a weight basis for the active fluorosucrose content. Although there is a slight variation in the molecular weight of the mono-, di- and tri-substituted derivatives of sucrose, calculating amounts to be used or concentrations on a mole basis is not essential for practicing this invention. However, if greater accuracy is desired, the amounts and concentrations set out above can be considered as being the preferred concentrations for a disubstituted sucrose (6,6'-difluorosucrose), and the corresponding concentration to be used for the other active fluorosucrose compounds can be computed on a molar equivalent basis. Inactive fluorosucrose compounds can be present but are not included in determining the amount to be used. The use of mixtures containing both active and inactive fluorosucroses are convenient for practicing the invention, because such mixtures are readily produced and need not be subjected to separation procedures.

The two difluorosucroses, 6,6'-dideoxy-6,6'-difluorosucrose and 1',6'-dideoxy-1',6'-difluorosucrose, and the trifluorosucrose, 6,1',6'-trideoxy-6,1',6'-trifluorosucrose are also believed to inhibit the biosynthesis of levan from sucrose by levansucrase. The enzyme levansucrase is also elaborated by oral bacteria, and has been postulated to also be involved in dental plaque and caries formation, although to a lesser extent than dextransucrase. See Higuchi et al, *Arch. Oral Biol.*, 15:563 (1970), and J. Carlson, *Caries Res.*, 4:97 (1970). The compounds 6,6'-difluorosucrose and 6,1',6'-trifluorosucrose appear capable of performing a dual function in preventing the formation of dental plaque.

EXAMPLE I

Preparation of Fluorosucrose Mixture (1) Preparation of 6,1',6'-tri-O-(2,4,6-triisopropylbenzenesulfonyl)-sucrose (A) hereafter referred to as tritripsylsucrose. This intermediate was prepared according to the method of Almquist and Reist, *J. Carbohydrates . Nuclelsides . Nucleotides*, 1:461 (1974).

Sucrose (52 g.) was dissolved in 750 ml of anhydrous pyridine by refluxing. The resulting solution was cooled to 0° C. and then mixed with 2,4,6-triisopropylbenzenesulfonylchloride (231.5 g). The cooling ice bath was removed and the resulting mixture was allowed to stand for four days at room temperature (25°–28° C.). The reaction mixture was then cooled to 0° C. again and 125 ml of water was added dropwise with constant stirring. The mixture was then stirred for 30 min. after the ice bath was removed. The resulting solution was reduced in volume to a yellow syrup by evaporation under reduced pressure at 50° C. The syrup was slurried with ethylacetate (500 ml), cooled to 0°, and filtered. The filter cake was washed with cold ethylacetate. The ethylacetate solutions were combined and washed successively with cold 2 N hydrochloric acid, saturated sodium bicarbonate, 4% saturated aqueous sodium chloride, and finally water. The ethyl acetate layer was dried over anhydrous calcium sulfate, filtered and evaporated under vacuo to dryness, forming a thick white foam (compound A).

(2) Preparation of 6,1',6'-tri-O-tripsyl-2,3,4,3'4'-penta-O-acetylsucrose (B)

The tritripsylsucrose (A) was dissolved in 200 ml pyridine and 160 ml of acetic anhydride was slowly added with cooling. The reaction mixture was stirred at 25°–28° C. for 24 hours. resulting solution was slowly added to 1.5 liters of crushed ice resulting in the formation of a thick gummy precipitate. The precipitate was dissolved in ethylacetate and washed with cold 2 N hydrochloric acid, followed by a saturated solution of sodium carbonate and finally water. The ethylacetate solution was dried over anhydrous sodium sulfate and then filtered and evaporated to dryness resulting in (B).

(3) Fluorination of Compound (B)

The pentaacetate (B) was dissolved in anhydrous dimethylformamide (250 ml) to which anhydrous potassium fluoride (90 g) was added. The resulting solution was refluxed for 24 hrs. and then poured into 3 liters of crushed ice. The resulting precipitate was dissolved in ethylacetate (2 liters) which was washed with 5 liters of 4% solution of sodium chloride. The organic layer was reduced in volume to a thick syrup (Compound C).

(4) Deacetylation of (C) and Formation of a Mixture of Fluorosucroses

The syrup (C) was dissolved in a minimum of dry methanol and then a few milliliters of a 1 M sodium methoxide solution in methanol was added to bring the final concentration of methoxide to 0.03 molar. The mixture was allowed to stand 12 hrs. at 27° C. and then was deionized by absorbing onto 500 g. of absorbent charcoal which was washed with 2–3 liters of distilled water and then with 1 liter of 10% t-butyl alcohol. The t-butyl alcohol solution was evaporated to a syrup which was further dried by azeotroping with ethanol and toluene. This syrup was the mixture of fluorosucroses which on thin layer chromatography indicated seven compounds which were 6-fluorosucrose, 6,6'-difluorosucrose, 6,1',6'-trifluorosucrose, 6,1'-difluorosucrose, 6',1'-difluorosucrose, 6'-fluorosucrose, 1'-fluorosucrose. From the relative amounts of the compounds, the content of the $C_6$-substituted active fluorosucroses was estimated as 60–75% by weight of the total mixture.

EXAMPLE II

Inhibition of Dextransucrase with a Mixture of Fluorosucroses

Dextransucrase was obtained from the culture supernatant of bacteria. Various amounts (6 to 30 mg/ml) of the fluorosucrose mixture prepared as in Example I were added to the enzyme (3 units/ml)* and allowed to incubate 10 minutes. At the end of this time, the enzyme was assayed by adding ½ volume of 0.3 M $^{14}C$-(U)-sucrose to the fluorosucrose-enzyme solution; equal aliquots were withdrawn with time and spotted onto 1.5×1.5 cm squares of Whatman 3 MM paper, which were immediately dropped into 20 ml anhydrous methanol. Three 200 ml volumes of methanol were added in 15 min. intervals. The papers were then removed, dried, and the radioactivity determined in a liquid scintillation spectrometer. The amount of radioactivity (polysaccharide formed) was plotted against the reaction time with sucrose (time of aliquot removed). The slopes of the resulting lines were determined and the percent inhibition calculated from the ratio of the slopes of the inhibited reactions to the slope of a control in which no inhibitor was added.

*Units are in terms of International Enzyme Units, that is, the amount of enzyme that will incorporate one micromole of monomer into polysaccharide per minute under conditions of optimum temperature and pH.

The results for the inhibition of dextransucrase by various concentrations of the fluorosucrose mixture are given in Table 1. It was determined that for dextransucrase 3 mg/ml of the fluorosucrose mixture did not produce any inhibition and that the minimum concentration to give 100 percent inhibition was 18.8 mg/ml.

Table 1

| Inhibition of dextransucrase by various concentrations of fluorosucrose mixtures | |
|---|---|
| mg/ml of Inhibitor | Percent Inhibition |
| 0 | 0 |
| 6.3 | 23.8 |
| 7.2 | 34.9 |
| 7.8 | 36.3 |
| 10.5 | 59.2 |
| 13.1 | 74.2 |
| 15.6 | 99.0 |
| 26.1 | 100.0 |

EXAMPLE III

Preparation of 6,1',6'-Trideoxy-6,1',6'-Trifluorosucrose

As the first step in the synthesis sucrose is subjected to tritylation by the method of Hough et al., *Carbohydrate Research* 21:144 (1972). This will result in a mixture containing tritanol, 6,1',6'-tri-O-tritylsucrose, 6,6'-di-O-tritylsucrose, 6,1'-di-O-tritylsucrose, 1',6'-di-O-tritylsucrose, 6- and 6'-mono-O-tritylsucrose, and some unreacted sucrose.

The first three compounds are the major components of this mixture. Separation of the components can be achieved by column chromatography on silica gel. Tritanol is eluted with chloroform; 6,1',6'-tri-O-tritylsucrose is eluted with chloroform:acetone (8:1 v/v) mixture; the three di-O-tritylsucroses are eluted together with chloroform:acetone (1:1 v/v) mixture; the two mono-O-tritylsucroses are eluted with methanol.

6,1',6'-tri-O-tritylsucrose is benzoylated using benzoyl chloride with anhydrous pyridine as a solvent and proton acceptor. The resulting 6,1',6'-tri-O-trityl-2,3,4,3',4'-penta-O-benzoylsucrose is purified by silica gel chromatography using benzene:diethylether (9:1 v/v) as eluting solvent. The tri-O-tritylpentabenzoate is then detritylated (see Hough et al, cited above), and purified on a silica gel column using chloroform:acetone (8:1 v/v) as eluting solvent to give 2,3,4,3',4'-penta-O-benzoylsucrose.

2,3,4,3',4'-penta-O-benzoylsucrose is fluorinated with N,N-diethylaminosulfurtrifluoride (DAST) in a modification of the procedure employed by Tewson and Welch on an allose derivative *Journal of Organic Chemistry*, 43:1090 (1978). 6,1',6'-trideoxy-6,1',6'-trifluoro-2,3,4,3',4'-penta-O-benzoylsucrose is purified by silica gel column chromatography; it is then treated with catalytic amounts of sodium methoxide in methanol. The resulting product is deionized with an acid-ion-exchange resin, and the methanol solution containing the product is filtered to remove the resin and evaporated to dryness. The dry foam is triturated with chloroform and water (1:1 v/v) to remove methylbenzoate. The product, 6,1',6-trideoxy-6,1',6'-trifluorosucrose is in the aqueous phase; evaporation of the aqueous phase resulted in the desired product as a solid.

EXAMPLE IV

Preparation of 6,6'-Dideoxy-6,6'-Difluorosucrose

Starting with the mixture of di-O-tritylsucroses which is eluted from the silica gel column as described in Example III, the 6,6'-di-O-tritylsucrose is purified by crystallization from a 4:1 methanol:water solution. See Otake, *Bulletin of the Chemical Society of Japan* 45:2895 (1972). This is benzoylated with benzoyl chloride, detritylated, fluorinated with DAST, and debenzoylated as described above for the preparation of the trifluorosucrose. This gives 6,6'-dideoxy-6,6'-difluorosucrose.

EXAMPLE V

Preparation of 6-deoxy-6-Fluorosucrose

Starting with the mixture of the mono-O-tritylsucroses which is eluted from the silica gel column described in Example III, 6-O-tritylsucrose is purified by crystallization from a 1:1 ethanol:water solution. See Otake, *Bulletin of the Chemical Society of Japan*, 43:3199 (1970). This is benzoylated with benzoyl chloride, detritylated, fluorinated with DAST and debenzoylated as described above for the preparation of the trifluorosucrose. This gives 6-deoxy-6-fluorosucrose.

EXAMPLE VI

In the following formulation examples, the inhibitor is a mixture of fluorosucroses prepared as described in Example I or a pure fluorosucrose as described in Examples III, IV, and V. The weight percents are on a total weight basis. However, it should be understood that a corresponding amount by weight (or a molar equivalent amount) of individual active fluorosucrose compounds or mixtures thereof can be substituted.

| Formula A Tooth Paste | |
|---|---|
| Ingredients | % by wt. |
| Glycerine | 19.95 |
| Carboxymethylcellulose | 1.14 |
| Sodium benzoate | 0.60 |
| Tetrasodium pyrophosphate | 0.35 |
| Deionized water | 20.63 |
| Dicalcium phosphate dihydrate | 46.38 |
| Calcium carbonate | 5.05 |
| Flavor | 0.90 |
| Fluorosucrose mixture (67% active), or individual fluorosucrose on corresponding weight basis | 5.00 |

| Formula B Tooth Powder | |
|---|---|
| Ingredients | % by wt. |
| Magnesium silicate | 7.00 |
| Dicalcium phosphate dihydrate | 85.50 |
| Flavor | 2.50 |
| Fluorosucrose mixture (67% active), or individual fluorosucrose on corresponding weight basis | 5.00 |

| Formula C Mouthwash | |
|---|---|
| Ingredients | % by wt. |
| Ethyl alcohol | 15.00 |
| Flavoring and coloring | 2.00 |
| Fluorosucrose mixture (67% active), or individual fluorosucrose on corresponding weight basis | 5.00 |
| Deionized water | 78.00 |

| Formula D Chewing Gum | |
|---|---|
| Ingredients | % by wt. |
| Gum base | 92.00 |
| Corn syrup | 5.00 |
| Flavors and colors | 1.00 |
| Fluorosucrose mixture (67% active), or individual fluorosucrose on corresponding weight basis | 2.00 |

| Formula E Tablet | |
|---|---|
| Ingredients | % by wt. |
| Mannitol | 94.00 |
| Flavor | 1.00 |
| Fluorosucrose mixture (67% active), or individual fluorosucrose on corresponding weight basis | 5.00 |

We claim:

1. The method of inhibiting dextransucrase synthesis of dextran from sucrose, comprising introducing into an aqueous substrate containing sucrose and dextransucrase an inhibitory amount of at least one fluorosucrose which has been substituted at least at the 6-position with a fluorine atom for the hydroxyl group.

2. The method of claim 1 in which said fluorosucrose is selected from the class consisting of 6-fluorosucrose, 6,1'-difluorosucrose, 6,6'-difluorosucrose, 6,1',6'-trifluorosucrose, and mixtures thereof.

3. The method of claim 1 in which said fluorosucrose is 6-fluorosucrose.

4. The method of claim 1 in which said fluorosucrose is 6,1'-difluorosucrose.

5. The method of claim 1 in which said fluorosucrose is 6,6'-difluorosucrose.

6. The method of claim 1 in which said fluorosucrose is 6,1',6'-trifluorosucrose.

7. The method of claim 1 in which said fluorosucrose comprises a mixture of 6-fluorosucrose, 6,1'-difluorosucrose, 6,6'-difluorosucrose, and 6,1',6'-trifluorosucrose.

8. An oral composition comprising a carrier suitable for use in the oral cavity containing an amount of at least one fluorosucrose effective for inhibiting the dextransucrase synthesis of dextran, said fluorosucrose having fluorine substituted for at least the $C_6$ hydroxyl.

9. The oral composition of claim 8 in which said fluorosucrose comprises a mixture of 6-fluorosucrose, 6,1'-difluorosucrose, 6,6'-difluorosucrose, 6,1',6'-trifluorosucrose, and mixtures thereof.

10. The oral composition of claim 8 in which said fluorosucrose is 6-fluorosucrose.

11. The oral composition of claim 8 in which said fluorosucrose is 6,1'-difluorosucrose.

12. The oral composition of claim 8 in which said fluorosucrose is 6,6'-difluorosucrose.

13. The oral composition of claim 8 in which said fluorosucrose is 6,1',6'-trifluorosucrose.

14. The oral composition of claim 8 in which said carrier is a toothpaste.

15. The oral composition of claim 8 in which said carrier is a toothpowder.

16. The oral composition of claim 8 in which said carrier is a chewing gum.

17. The oral composition of claim 8 in which said carrier is a water soluble tablet.

18. The oral composition of claim 8 in which said carrier is a mouthwash.

19. A toothpaste containing from 1 to 5 weight percent of $C_6$-substituted fluorosucrose selected from the class consisting of 6-fluorosucrose, 6,1'-difluorosucrose, 6,6'-difluorosucrose, and 6,1',6'-trifluorosucrose, and mixtures thereof.

20. A mouthwash containing from 20 to 30 grams per liter of $C_6$-substituted fluorosucrose selected from the class consisting of 6-fluorosucrose, 6,1'-difluorosucrose, 6,6'-difluorosucrose, and 6,1',6'-trifluorosucrose, and mixtures thereof.

21. Water soluble tablets suitable for use in the mouth, containing from 1 to 5 weight percent per table of $C_6$-substituted fluorosucrose selected from the class consisting of 6-fluorosucrose, 6,1'-difluorosucrose, 6,6'-difluorosucrose, and 6,1',6'-trifluorosucrose, and mixtures thereof.

22. Chewing gum in stick form containing from 1 to 5 weight percent of $C_6$-substituted fluorosucrose selected from the class consisting of 6-fluorosucrose, 6,1'-difluorosucrose, 6,6'-difluorosucrose, and 6,1',6'-trifluorosucrose, and mixtures thereof.

23. 6-fluorosucrose.

24. 6,1'-difluorosucrose.

25. 6,6'-difluorosucrose.

26. 6,1',6'-trifluorosucrose.

* * * * *